(12) United States Patent
Kunzler et al.

(10) Patent No.: US 7,544,371 B2
(45) Date of Patent: Jun. 9, 2009

(54) DRUG DELIVERY SYSTEMS

(75) Inventors: Jay Kunzler, Canandaigua, NY (US);
Joseph Salamone, Boca Raton, FL (US)

(73) Assignee: Bausch + Lomb Incorporated, Rochester, NY (US)

( * ) Notice: Subject to any disclaimer, the term of this patent is extended or adjusted under 35 U.S.C. 154(b) by 457 days.

(21) Appl. No.: 11/311,983

(22) Filed: Dec. 20, 2005

(65) Prior Publication Data
US 2007/0141115 A1    Jun. 21, 2007

(51) Int. Cl.
*A61K 9/14* (2006.01)
*A61F 2/00* (2006.01)

(52) U.S. Cl. .................. 424/484; 424/427; 424/486

(58) Field of Classification Search ............... 424/427, 424/486, 484
See application file for complete search history.

(56) References Cited

U.S. PATENT DOCUMENTS

| | | | |
|---|---|---|---|
| 4,153,641 A | 5/1979 | Deichert et al. |
| 4,192,827 A | 3/1980 | Mueller et al. |
| 4,486,577 A | 12/1984 | Mueller et al. |
| 4,605,712 A | 8/1986 | Mueller et al. |
| 4,954,587 A | 9/1990 | Mueller |
| 5,260,000 A | 11/1993 | Nandu et al. |
| 5,273,530 A | 12/1993 | del Cerro et al. |
| 5,310,779 A | 5/1994 | Lai |
| 5,387,662 A | 2/1995 | Kunzler et al. |
| 5,409,457 A | 4/1995 | del Cerro et al. |
| 5,449,729 A | 9/1995 | Lai |
| 5,512,205 A | 4/1996 | Lai |
| 5,610,252 A | 3/1997 | Bambury et al. |
| 5,616,757 A | 4/1997 | Bambury et al. |
| 5,710,302 A | 1/1998 | Kunzler et al. |
| 5,714,557 A | 2/1998 | Kunzler et al. |
| 5,908,906 A | 6/1999 | Kunzler et al. |
| 6,891,010 B2 | 5/2005 | Kunzler et al. |
| 2002/0002362 A1 | 1/2002 | Humayun et al. |
| 2004/0043067 A1 | 3/2004 | Salamone et al. |
| 2004/0253293 A1 | 12/2004 | Shafiee et al. |

*Primary Examiner*—Raymond J Henley, III
(74) *Attorney, Agent, or Firm*—Glenn D. Smith

(57) ABSTRACT

Matrix controlled diffusion drug delivery systems based on one or more silicone-containing monomers of the general formula:

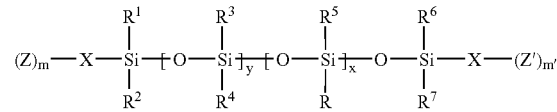

wherein x, y, m, m', R, $R^1$, $R^2$, $R^3$, $R^4$, $R^5$, $R^6$, $R^7$, X, Z and Z' are as defined herein are provided, wherein the matrix controlled diffusion drug delivery systems are sized and configured for back of the eye delivery.

10 Claims, 2 Drawing Sheets

DRUG DELIVERY SYSTEMS

BACKGROUND OF THE INVENTION

1. Technical Field

The present invention relates generally to hydrogels, drug delivery systems, and methods of treatment.

2. Description of Related Art

Conventional drug delivery involving frequent periodic dosing is not ideal or practical in many instances. For example, with more toxic drugs, conventional periodic dosing can result in high initial drug levels at the time of dosing, followed by low drug levels between doses often times below levels of therapeutic value. Likewise, conventional periodic dosing may not be practical or therapeutically effective in certain instances such as with pharmaceutical therapies targeting areas of the inner eye or brain in need of treatment such as the retina.

During the last two decades, significant advances have been made in the design of controlled release drug delivery systems. See, e.g., U.S. Patent Application Publication Nos. 2004/0043067 and 2004/0253293. Such advances have been made in an attempt to overcome some of the drug delivery shortcomings noted above. In general, controlled release drug delivery systems include both sustained drug delivery systems designed to deliver a drug for a predetermined period of time, and targeted drug delivery systems designed to deliver a drug to a specific area or organ of the body. Sustained and/or targeted controlled release drug delivery systems may vary considerably by mode of drug release within three basic drug controlled release categories. Basic drug controlled release categories include diffusion controlled release, chemical erosion controlled release and solvent activation controlled release. In a diffusion controlled release drug delivery system, a drug is surrounded by an inert barrier and diffuses from an inner reservoir, or a drug is dispersed throughout a polymer and diffuses from the polymer matrix. In a chemical erosion controlled release drug delivery system, a drug is uniformly distributed throughout a biodegradable polymer. The biodegradable polymer is designed to degrade as a result of hydrolysis to then uniformly release the drug. In a solvent activation controlled release drug delivery system, a drug is immobilized on polymers within a drug delivery system. Upon solvent activation, the solvent sensitive polymer degrades or swells to release the drug. Unfortunately, controlled release drug delivery systems to date do not provide a means by which one may manipulate and control drug delivery systems' drug release rate for specific drugs over a broad range of drugs.

Because of the noted shortcomings of current controlled release drug delivery systems, a need exists for controlled release drug delivery systems that allow for manipulation and control of drug release rates depending on the drug to be delivered, the location of delivery, the purpose of delivery and/or the therapeutic requirements of the individual patient.

SUMMARY OF THE INVENTION

In accordance with one embodiment of the present invention, a matrix controlled diffusion drug delivery system comprising a therapeutically effective amount of one or more pharmaceutically active agents entrapped in a polymerization product of a monomeric mixture comprising one or more silicone-containing monomers of the general formula:

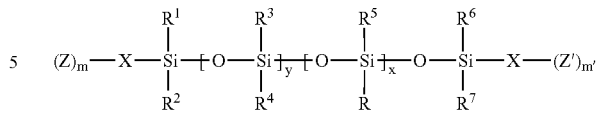

wherein x, y, m, m', R, $R^1$, $R^2$, $R^3$, $R^4$, $R^5$, $R^6$, $R^7$, X, Z and Z' are as defined herein, wherein the matrix controlled diffusion drug delivery system is sized and configured for back of the eye delivery.

In accordance with a second embodiment of the present invention, a process for preparing a matrix controlled diffusion drug delivery system sized and configured for back of the eye delivery is provided, the process comprising entrapping a therapeutically effective amount of one or more pharmaceutically active agents in a polymerization product of a monomeric mixture comprising one or more silicone-containing monomers of the general formula:

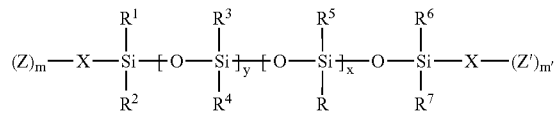

wherein x, y, m, m', R, $R^1$, $R^2$, $R^3$, $R^4$, $R^5$, $R^6$, $R^7$, X, Z and Z' are as defined herein.

In accordance with a third embodiment of the present invention, a process for preparing a matrix controlled diffusion drug delivery system sized and configured for back of the eye delivery is provided, the process comprising (a) swelling a polymerization product of a monomeric mixture comprising one or more silicone-containing monomers of the general formula:

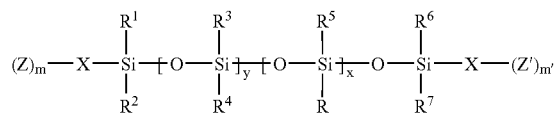

wherein x, y, m, m', R, $R^1$, $R^2$, $R^3$, $R^4$, $R^5$, $R^6$, $R^7$, X, Z and Z' are as defined herein, in a swelling solution comprising one or more solvents and a therapeutically effective amount of one or more pharmaceutically active agents; and (b) removing the polymerization product from the solution to provide the matrix controlled diffusion drug delivery system comprising the therapeutically effective amount of one or more pharmaceutically active agents entrapped in the polymerization product.

In accordance with a fourth embodiment of the present invention, a process for preparing a matrix controlled diffusion drug delivery system sized and configured for back of the eye delivery is provided, the process comprising polymerizing a monomeric mixture comprising one or more silicone-containing monomers of the general formula:

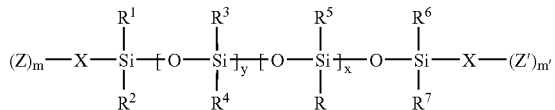

wherein x, y, m, m', R, $R^1$, $R^2$, $R^3$, $R^4$, $R^5$, $R^6$, $R^7$, X, Z and Z' are as defined herein, in the presence of a therapeutically effective amount of one or more pharmaceutically active agents to provide the matrix controlled diffusion drug delivery system comprising the therapeutically effective amount of one or more pharmaceutically active agents entrapped in the polymerization product.

In accordance with a fifth embodiment of the present invention, a method of treating an ophthalmic state, disease, disorder, injury or condition is provided, the method comprising administering to a mammal in need of such treatment a matrix controlled diffusion drug delivery system comprising a therapeutically effective amount of one or more pharmaceutically active agents entrapped in a polymerization product of a monomeric mixture comprising one or more silicone-containing monomers of the general formula:

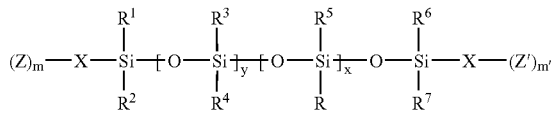

wherein x, y, m, m', R, $R^1$, $R^2$, $R^3$, $R^4$, $R^5$, $R^6$, $R^7$, X, Z and Z' are as defined herein, wherein the matrix controlled diffusion drug delivery system is sized and configured for back of the eye delivery.

The drug delivery systems of the present invention may advantageously be designed to allow for manipulation and control of drug release rates, which may be based on the drug to be delivered, the location of delivery, the purpose of delivery and/or the therapeutic requirements of the individual patient such that treatment of a disease, disorder or injury in a mammal may be achieved. The matrix controlled diffusion drug delivery system are also advantageously sized and configured for back of the eye delivery of the one or more pharmaceutically active agents.

The term "monomer" and like terms as used herein denote relatively low molecular weight compounds that are polymerizable by, for example, free radical polymerization, as well as higher molecular weight compounds also referred to as "prepolymers", "macromonomers", and related terms. Accordingly, it is to be understood that the term "silicon-containing monomer(s) include corresponding prepolymers.

The term "(meth)" as used herein denotes an optional methyl substituent. Accordingly, terms such as "(meth)acrylate" denotes either methacrylate or acrylate, and "(meth) acrylic acid" denotes either methacrylic acid or acrylic acid.

The term "treating" or "treatment" of a state, disease, disorder, injury or condition as used herein shall be understood to mean (1) preventing or delaying the appearance of clinical symptoms of the state, disease, disorder, injury or condition developing in a mammal that may be afflicted with or predisposed to the state, disease, disorder, injury or condition but does not yet experience or display clinical or subclinical symptoms of the state, disease, disorder, injury or condition, (2) inhibiting the state, disease, disorder, injury or condition, i.e., arresting or reducing the development of the disease or at least one clinical or subclinical symptom thereof, or (3) relieving the state, disease, disorder, injury or condition, i.e., causing regression of the state, disease, disorder, injury or condition or at least one of its clinical or subclinical symptoms.

The term "delivering" as used herein shall be understood to mean providing a therapeutically effective amount of a pharmaceutically active agent to a particular location within a host causing a therapeutically effective concentration of the pharmaceutically active agent at the particular location.

The term "subject" or "patient" or "host" or "mammal" as used herein refers to mammalian animals and humans.

DETAILED DESCRIPTION OF THE PREFERRED EMBODIMENTS

Figure 1:
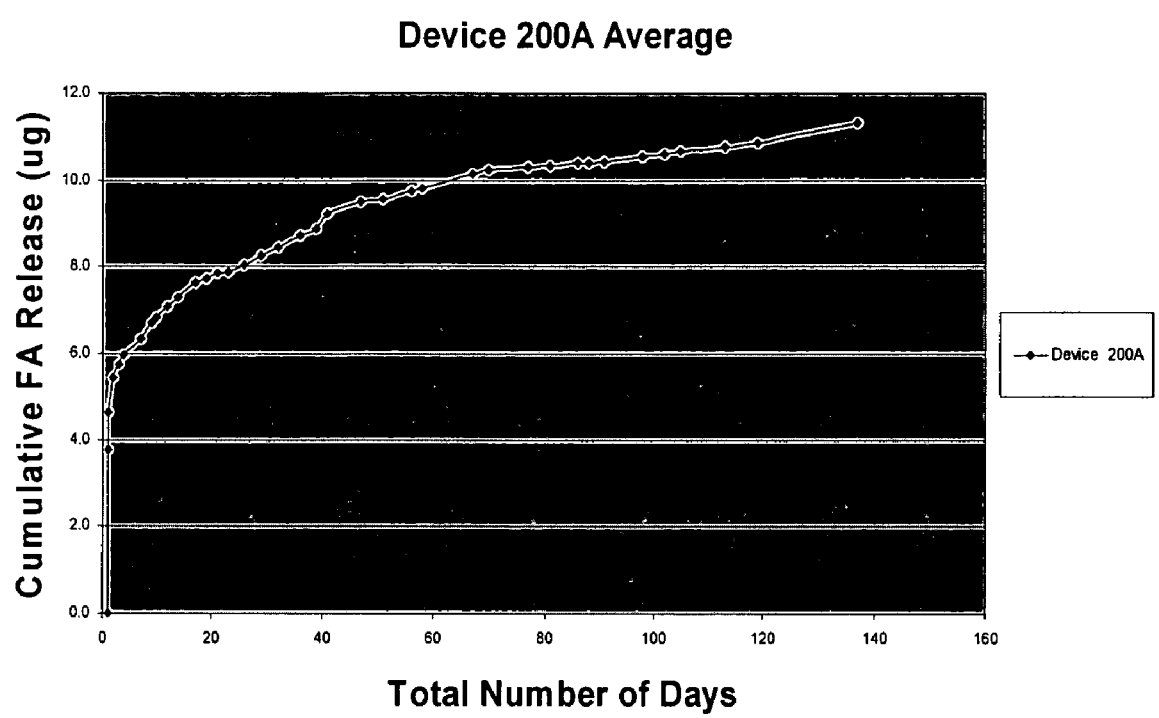
FIG. 1 is a graphical representation depicting the percent cumulative drug release rate over time for a $M_2D_2$ (200A) siloxane loaded with 30% w/w fluocinolone acetonide.

The present invention relates to matrix controlled diffusion drug delivery systems based on one or more silicone-containing monomers and are sized and configured for back of the eye drug delivery for the treatment of a state, disease, disorder, injury or condition in a mammal in need of treatment such as an ophthalmic disease in a mammal. The subject matrix controlled diffusion drug delivery systems advantageously allow for manipulation and control of drug release rates which may be based on, for example, the drug to be delivered, the location of delivery, the purpose of delivery and/or the therapeutic requirements of the individual patient. The rate of release of the pharmaceutically active agents can be controlled by manipulating the hydrophobic/hydrophilic balance of the silicone-containing monomer(s) to achieve the desired rate of drug release.

The monomeric mixtures for use in forming the matrix controlled diffusion drug delivery systems of the present invention will include at least one or more silicone-containing monomers represented by the general formula I:

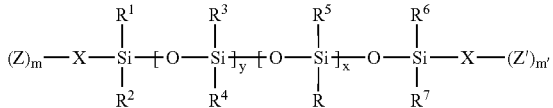

wherein x and y are independently integers from 0 to about 300; m and m' are independently integers from 1 to about 6, R is independently a straight or branched, substituted or unsubstituted, $C_1$-$C_{30}$ alkyl group, a $C_1$-$C_{30}$ fluoroalkyl group, an alkyl ether, cycloalkyl ether, cycloalkylalkyl ether, cycloalkenyl ether, aryl ether, arylalkyl ether or a polyether containing group or a $C_1$-$C_{30}$ alkylamide group, $R^1$, $R^2$, $R^3$, $R^4$, $R^5$, $R^6$ and $R^7$ are independently hydrogen, a straight or branched $C_1$-$C_{30}$ alkyl group, a $C_1$-$C_{30}$ fluoroalkyl group, a $C_1$-$C_{20}$ ester group, an alkyl ether, cycloalkyl ether, cycloalkylalkyl ether, cycloalkenyl ether, aryl ether, arylalkyl ether or polyether containing group, an ureido group, an amide group, an amine group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocyclolalkyl group, a substituted or unsubstituted $C_6$-$C_{30}$ heteroarylalkyl group, fluorine, a vinyl group, a $C_5$-$C_{30}$ fluoroaryl group, or a hydroxyl group; X is independently a bond, a straight or branched $C_1$-$C_{30}$ alkyl group, a $C_1$-$C_{30}$ fluoroalkyl group, a substituted or unsubstituted $C_5$-$C_{30}$ arylalkyl group, a substituted or unsubstituted $C_1$-$C_{30}$ alkoxy group, an ether, polyether, sulfide, or amino-containing group and Z and Z' are independently a polymerizable ethylenically unsaturated organic radical.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl(isopropyl), n-butyl, n-pentyl, etc., and the like.

Representative examples of fluoroalkyl groups for use herein include, by way of example, a straight or branched alkyl group as defined above having one or more fluorine atoms attached to the carbon atom, e.g., $-CF_3$, $-CF_2CF_3$, $-CH_2CF_3$, $-CH_2CF_2H$, $-CF_2H$ and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are defined above, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula $-R^8OR^9$, wherein $R^8$ is a bond, an alkyl, cycloalkyl or aryl group as defined above and $R^9$ is an alkyl, cycloalkyl or aryl group as defined above, e.g., $-CH_2CH_2OC_6H_5$ and $-CH_2CH_2OC_2H_5$, and the like.

Representative examples of amide groups for use herein include, by way of example, an amide of the general formula $-R^{10}C(O)NR^{11}R^{12}$ wherein $R^{10}$, $R^{11}$ and $R^{12}$ are independently $C_1$-$C_{30}$ hydrocarbons, e.g., $R^{10}$ can be alkylene groups, arylene groups, cycloalkylene groups and $R^{11}$ and $R^{12}$ can be alkyl groups, aryl groups, and cycloalkyl groups as defined herein and the like.

Representative examples of amine groups for use herein include, by way of example, an amine of the general formula $-R^{13}NR^{14}R^{15}$ wherein $R^{13}$ is a $C_2$-$C_{30}$ alkylene, arylene, or cycloalkylene and $R^{14}$ and $R^{15}$ are independently $C_1$-$C_{30}$ hydrocarbons such as, for example, alkyl groups, aryl groups, or cycloalkyl groups as defined herein, or a quaternary ammonium compound of the general formula

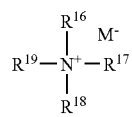

wherein $R^{16}$, $R^{17}$, $R^{18}$ and $R^{19}$ are independently $C_1$-$C_{30}$ hydrocarbons such as, for example, alkyl groups, aryl groups, or cycloalkyl groups as defined herein and M is an anion, and the like.

Representative examples of an ureido group for use herein include, by way of example, an ureido group having one or more substituents or unsubstituted ureido. The ureido group preferably is an ureido group having 1 to 12 carbon atoms. Examples of the substituents include alkyl groups and aryl groups. Examples of the ureido group include 3-methylureido, 3,3-dimethylureido, and 3-phenylureido.

Representative examples of alkoxy groups for use herein include, by way of example, an alkyl group as defined above attached via oxygen linkage to the rest of the molecule, i.e., of the general formula $-OR^{20}$, wherein $R^{20}$ is an alkyl, cycloalkyl, cycloalkylalkyl, cycloalkenyl, aryl or an arylalkyl as defined above, e.g., $-OCH_3$, $-OC_2H_5$, or $-OC_6H_5$, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronapthyl, adamantyl and norbornyl groups bridged cyclic group or spriro-bicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 18 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., $-CH_2C_6H_5$, $-C_2H_5C_6H_5$ and the like, wherein the aryl group can optionally contain one or more heteroatoms, e.g., O and N, and the like.

Representative examples of fluoroaryl groups for use herein include, by way of example, an aryl group as defined above having one or more fluorine atoms attached to the aryl group.

Representative examples of heterocyclic ring groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof.

Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quatemized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined above. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined above directly bonded to an alkyl group as defined above. The heteroarylalkyl radical may be attached to the main structure at any carbon atom from the alkyl group that results in the creation of a stable structure.

Representative examples of heterocyclo groups for use herein include, by way of example, a substituted or unsubstituted heterocylic ring radical as defined above. The heterocyclo ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined above directly bonded to an alkyl group as defined above. The heterocycloalkyl radical may be attached to the main structure at carbon atom in the alkyl group that results in the creation of a stable structure.

Representative examples of a "polymerizable ethylenically unsaturated organic radicals" include, by way of example, (meth)acrylate-containing radicals, (meth)acrylamide-containing radicals, vinylcarbonate-containing radicals, vinylcarbamate-containing radicals, styrene-containing radicals and the like or a polymerizable ethylenically unsaturated organic radical represented by the general formula:

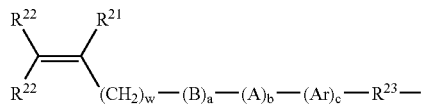

wherein $R^{21}$ is hydrogen or methyl; $R^{22}$ is independently hydrogen, an alkyl radical having 1 to 6 carbon atoms, or a —CO—Y—$R^{24}$ radical wherein Y is —O—, —S— or —NH—; $R^{24}$ is a divalent alkylene radical having 1 to about 10 carbon atoms; $R^{23}$ is an alkyl radical having 1 to about 12 carbon atoms; B denotes —CO— or —OCO—; A denotes —O— or —NH—; Ar denotes an aromatic radical having 6 to about 30 carbon atoms; w is 0 to 6; a is 0 or 1; b is 0 or 1; and c is 0 or 1.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' and 'substituted carboxylic acid derivative' may be the same or different with one or more selected from the group such as hydrogen, hydroxy, halogen, carboxyl, cyano, nitro, oxo(=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, substituted or unsubstituted guanidine, —COOR$_x$, —C(O)R$_x$, —C(S)R$_x$, —C(O)NR$_x$R$_y$, —C(O)ONR$_x$R$_y$, —NR$_x$CONR$_y$R$_z$, —N(R$_x$)SOR$_y$, —N(R$_x$)SO$_2$R$_y$, —(=N—N(Rx)R$_y$), —NR$_x$C(O)OR$_y$, —NR$_x$R$_y$, —NR$_x$C(O)R$_y$—, —NR$_x$C(S) R$_y$—NR$_x$C(S)NR$_y$R$_z$, —SONR$_x$R$_y$—, —SO$_2$NR$_x$R$_y$—, —OR$_x$, —OR$_x$C(O)NR$_y$R$_z$, —OR$_x$C(O)OR$_y$—, —OC(O)R$_x$, —OC(O)NR$_x$R$_y$, —R$_x$NR$_y$C(O)R$_z$, —R$_x$OR$_y$, —R$_x$C(O)OR$_y$, —R$_x$C(O)NR$_y$R$_z$, —R$_x$C(O)R$_x$, —R$_x$OC(O)R$_y$, —SR$_x$, —SOR$_x$, —SO$_2$R$_x$, —ONO$_2$, wherein R$_x$, R$_y$ and R$_z$ in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

In one embodiment, in the silicone-containing monomer x is from 1 to about 300 and preferably from about 20 to about 200, y is from 1 to about 300 and preferably from about 20 to about 200, each R is independently a straight or branched $C_1$-$C_{30}$ alkyl group, a straight or branched $C_1$-$C_{30}$ fluoroalkyl group, an alkyl ether or polyether containing group and a straight or branched $C_1$-$C_{30}$ alkylamide group, $R^1$, $R^2$, $R^3$, $R^4$, $R^5$, $R^6$ and $R^7$ are independently a straight or branched, saturated or unsaturated $C_1$-$C_{30}$ alkyl group and preferably a $C_1$-$C_6$ alkyl group, X is independently one or more $C_1$-$C_{30}$ alkyl ether groups and Z and Z' are (meth)acrylate-containing radicals. In one embodiment, a silicon-containing monomer(s) is represented by the general formula II:

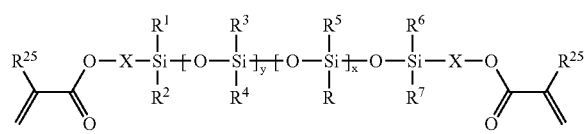

wherein x, y, R, $R^1$, $R^2$, $R^3$, $R^4$, $R^5$, $R^6$, $R^7$ and X have the aforestated meanings and $R^{25}$ is independently hydrogen or methyl.

Applicable silicon-containing monomers of formulae I and II employed in the monomeric mixtures for use in the drug delivery systems of the present invention are well known in the art and may be synthesized by known techniques and does not constitute a part of the present invention. Numerous examples of such silicon-containing monomers are provided in, e.g., U.S. Pat. No. 4,153,641 (Deichert et al.), U.S. Pat. No. 5,260,000 (Nandu et al.); U.S. Pat. No. 5,310,779 (Lai); U.S. Pat. No. 5,387,662 (Kunzler et al.); U.S. Pat. No. 5,449,729 (Lai); U.S. Pat. No. 5,512,205 (Lai); U.S. Pat. No. 5,610,252 (Bambury et al.); U.S. Pat. No. 5,616,757 (Bambury et al.); U.S. Pat. No. 5,710,302 (Kunzler et al.); U.S. Pat. No. 5,714,557 (Kunzler et al.); U.S. Pat. No. 5,908,906 (Kunzler et al.); and U.S. Pat. No. 6,891,010 (Kunzler et al.), the disclosures of which are incorporated herein by reference. For example, the silicon-containing monomers can be prepared as generally represented in Scheme 1 below:

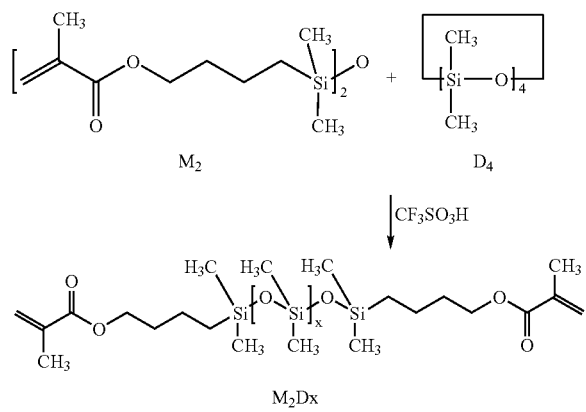

Although the monomeric mixtures containing the forgoing ethylenically terminated silicone-containing monomers can form a crosslinked three-dimensional network when polymerized, a wide variety of additional monomers may be added to the monomer mixture to provide alternative polymerization products, e.g., copolymers in random or block sequences, having a wide range of properties depending on the desired drug delivery systems. Examples of additional monomers and prepolymers include crosslinking agents such as polyvinyl, typically di- or tri-vinyl monomers, most commonly the di- or tri(meth)acrylates of dihydric ethylene glycol, triethylene glycol, butylene glycol, hexane-1,6-diol, thiodiethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N,N-methylene-bis-(meth)acrylamide, sulfonated divinylbenzene, and divinylsulfone. Also useful are the reaction products of hydroxyalkyl(meth)acrylates with unsaturated isocyanates, for example the reaction product of 2-hydroxyethyl methacrylate with 2-isocyanatoethyl methacrylate (IEM) as disclosed in U.S. Pat. No. 4,954,587.

Other known crosslinking agents are polyether-bisurethane-dimethacrylates as described in U.S. Pat. No. 4,192,827, and those crosslinkers obtained by reaction of polyethylene glycol, polypropylene glycol and polytetramethylene glycol with 2-isocyanatoethyl methacrylate (IEM) or m-isopropenyl-gamma,gamma,-dimethylbenzyl isocyanates (m-TMI), and polysiloxane-bisurethane-dimethacrylates as described in U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with about 0.1 to about 10 mol % vinyl isocyanates such as IEM or m-TMI.

Yet other examples include, but are not limited to, hydrophobic and hydrophilic monomers such as methyl methacrylate, 2-ethylhexyl methacrylate, benzyl methacrylate, 2-phenylethyl methacrylate, dimethyl itaconate, trifluoromethyl methacrylate, hexafluoroisopropyl methacrylate, bis(hexafluoroisopropyl) methacrylate, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxypoly(ethylene glycol) methacrylate, methacrylic acid, acrylic acid, itaconic acid, acrylic anhydride, methacrylic anhydride, maleic anhydride, itaconic anhydride, glycerol methacrylate, hydroxypropyl methacrylate, N,N-dimethylacrylamide, acrylamide, N-methylacrylamide, N-vinylpyrrolidione, N-isopropylacrylamide, hydroxybutyl methacrylate and the like and mixtures thereof.

In one embodiment, a monomeric mixture can contain from about 1 to about 50 weight percent and preferably from about 5 to about 20 weight percent of monomeric units represented by formula I, from about 10 to about 89 weight percent and preferably about 25 to about 50 weight percent of silicone-containing monomeric units other than those represented by formula I, and from about 10 to about 70 weight percent and preferably from about 20 to about 60 weight percent of hydrophilic or hydrophobic monomeric units.

Polymerization of the monomeric mixture can be carried out in any known manner. For example, the component(s) in the reaction mixture can be added continuously to a stirred reactor or can take place in a tubular reactor in which the components can be added at one or more points along the tube. In one embodiment, polymerization may be carried out at a temperature of from about 20° C. to about 100° C. and for a time sufficient to polymerize the silicone-containing monomers(s) and optional monomer(s), e.g., from about 5 minutes to about 16 hours.

In another embodiment, polymerization can be carried out by exposing the reactive monomer(s) to, for example, ultraviolet (UV) or visible light or electron beams, in the presence of one or more photoinitiator(s). The use of UV or visible light in combination with photoinitiators is well known in the art and is particularly suitable for formation of the polymerization product. Suitable photoinitiators which are useful for polymerizing the polymerizable mixture of monomers can be commercially available photoinitiators, e.g., photoinitiators commercially available under the "IRGACURE", "DAROCUR" and "SPEEDCURE" trade names (manufactures by Ciba Specialty Chemicals, also obtainable under a different name from BASF, Fratelli Lamberti and Kawaguchi). They are generally compounds which are capable of initiating the radical reaction of olefinically unsaturated double bonds on exposure to light with a wavelength of, for example, about 260 to about 480 mn.

Generally, pharmaceutically active agents or drugs useful in the matrix controlled diffusion drug delivery systems of the present invention can be any compound, composition of matter, or mixtures thereof that can be delivered from the drug delivery system to produce a beneficial and useful result to, for example, the eye, especially an agent effective in obtaining a desired local or systemic physiological or pharmacological effect. Examples of such agents include, but are not limited to, anesthetics and pain killing agents such as lidocaine and related compounds, benzodiazepam and related compounds and the like; anti-cancer agents such as 5-fluorouracil, adriamycin and related compounds and the like; anti-fungal agents such as fluconazole and related compounds and the like; anti-viral agents such as trisodium phosphomonoformate, trifluorothymidine, acyclovir, ganciclovir, DDI, AZT and the like; cell transport/mobility impending agents such as colchicine, vincristine, cytochalasin B and related compounds and the like; antiglaucoma drugs such as beta-blockers, e.g., timolol, betaxolol, atenalol, and the like; antihypertensives; decongestants such as phenylephrine, naphazoline, tetrahydrazoline and the like; immunological response modifiers such as muramyl dipeptide and related compounds and the like; peptides and proteins such as cyclosporin, insulin, growth hormones, insulin related growth factor, heat shock proteins and related compounds and the like; steroidal compounds such as dexamethasone, prednisolone and related compounds and the like; low solubility steroids such as fluocinolone acetonide and related compounds and the like; carbonic anhydrase inhibitors; diagnostic agents; antiapoptosis agents; gene therapy agents; sequestering agents; reductants such as glutathione and the like; antipermeability agents; antisense compounds; antiproliferative agents; antibody conjugates; antidepressants; bloodflow enhancers; antiasthmatic drugs; antiparasiticagents; non-steroidal anti inflammatory agents such as ibuprofen and the like; nutrients and vitamins: antioxidants; enzyme inhibitors: anticataract drugs; aldose reductase inhibitors; cytoprotectants; cytokines, cytokine inhibitors, and cytokin protectants; uv blockers; mast cell stabilizers; anti neovascular agents such as antiangiogenic agents, e.g., matrix metalloprotease inhibitors and the like.

Representative examples of additional pharmaceutically active agent for use herein include, but are not limited to, neuroprotectants such as nimodipine and related compounds and the like; antibiotics such as tetracycline, chlortetracycline, bacitracin, neomycin, polymyxin, gramicidin, oxytetracycline, chloramphenicol, gentamycin, erythromycin and the like; anti-infectives; antibacterials such as sulfonamides, sulfacetamide, sulfamethizole, sulfisoxazole; nitrofurazone, sodium propionate and the like; antiallergenics such as antazoline, methapyriline, chlorpheniramine, pyrilamine, prophenpyridamine and the like; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triminolone and the like; miotics; anti-cholinesterase such as pilocarpine, eserine salicylate, carbachol, di-isopropyl fluorophosphate, phospholine iodine, demecarium bromide and the like; miotic agents; mydriatics such as atropine sulfate, cyclopentolate, homatropine, scopolamine, tropicamide, eucatropine, hydroxyamphetamine and the like; svmpathomimetics such as epinephrine and the like; and prodrugs such as, for example, those described in Design of Prodrugs, edited by Hans Bundgaard, Elsevier Scientific Publishing Co., Amsterdam, 1985. In addition to the foregoing agents, other agents suitable for treating, managing, or diagnosing conditions in a mammalian organism may be entrapped in the copolymer and administered using the drug delivery systems of the current invention. Once again, reference may be made to any standard pharmaceutical textbook such as, for example, Remington's Pharmaceutical Sciences for pharmaceutically active agents.

Any pharmaceutically acceptable form of the foregoing pharmaceutically active agent may be employed in the practice of the present invention, e.g., the free base; free acid; pharmaceutically acceptable salts, esters or amides thereof, e.g., acid additions salts such as the hydrochloride, hydrobromide, sulfate, bisulfate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulfate salts and the like; alkali or alkaline earth metal salts such as the sodium, calcium, potassium and magnesium salts and the like; hydrates; enantiomers; isomers; stereoisomers; diastereoisomers; tautomers; polymorphs, mixtures thereof, prodrugs thereof or racemates or racemic mixtures thereof.

Actual dosage levels of the pharmaceutically active agent (s) in the drug delivery systems of the present invention may be varied to obtain an amount of the pharmaceutically active agent(s) that is effective to obtain a desired therapeutic response for a particular system and method of administration. The selected dosage level therefore depends upon such factors as, for example, the desired therapeutic effect, the route of administration, the desired duration of treatment, and other factors. The total daily dose of the pharmaceutically active agent(s) administered to a host in single or divided doses can vary widely depending upon a variety of factors including, for example, the body weight, general health, sex, diet, time and route of administration, rates of absorption and excretion, combination with other drugs, the severity of the particular condition being treated, etc. Generally, the amounts of pharmaceutically active agent(s) present in the drug delivery systems of the present invention can range from about 0.1% w/w to about 60% w/w and preferably from about 1% w/w to about 50% w/w.

Polymerization products of the monomeric mixtures containing at least one or more of the silicon-containing monomers may be combined with one or more pharmaceutically active agents to form the drug delivery systems of the present invention. By controlling the concentration of the hydrophobic and hydrophilic groups on the siloxane backbone, hydrophobic and hydrogen-bonding interactions with the drug can occur. For example, if fluoroalkyl pendant groups on the siloxane polymer are present, greater solubility of a fluorinated drug in the polymer matrix will be realized, thus giving longer sustained delivery of the drug. If this enhanced solubility of drug is incorporated with added hydrophilic hydrogen bonding, the sustained release characteristics of the drug will be further enhanced. Additionally, if the siloxane polymer contains hydrophilic anionic sites, such as from carboxylic acid groups, these anionic groups can ionically interact with cationic drugs, thus slowing and extending the release of drug. The hydrophobic/hydrophilic balance of characteristics may thus be manipulated to achieve the desired rate of drug release. The desired rate of drug release may be determined based on the drug to be delivered, the location of delivery, the purpose of delivery and/or the therapeutic requirements of the individual patient. The hydrophobic/hydrophilic balance of characteristics dictates the solubility of the drug, and is a primary factor controlling the rate of drug release.

Generally, the drug delivery systems of the present invention can be prepared by first forming the polymerization product of a monomeric mixture as described hereinabove and then entrapping a therapeutically effective amount of one or more of pharmaceutically active agents therein. In one embodiment, the process may include at least (a) forming a polymerization product of a monomeric mixture as described hereinabove; (b) swelling the polymerization product in a swelling solution comprising one or more solvents and a therapeutically effective amount of at least one pharmaceutically active agent; and (c) removing the polymerization product from the solution to provide the matrix controlled diffusion drug delivery system comprising the therapeutically effective amount of one or more pharmaceutically active agents entrapped in the polymerization product.

In step (b) of the process, the polymerization product can be swelled with the swelling solution by, for example, immersing the polymerization product in the swelling solution for a time period sufficient to entrap the pharmaceutically active agent in the polymerization product, e.g., a time period of from about 1 hour to about 24 hours. The swelling solution will ordinarily include at least one or more solvents and a therapeutically effective amount of the one or more pharmaceutically active agents. Suitable solvents include, but are not limited to, ketones, alcohols, ethers, aliphatic hydrocarbons, aromatic hydrocarbons, sulfoxides, amide-based solvents and the like and mixtures thereof.

Suitable ketones for use herein can be one or more ketones of the general formula $R^{26}R^{27}C(O)$ wherein $R^{26}$ and $R^{27}$ are the same or different and can be a substituted or unsubstituted $C_1$-$C_{30}$ alkyl, a substituted or unsubstituted $C_3$-$C_{30}$ cycloalkyl, a substituted or unsubstituted $C_3$-$C_{30}$ cycloalkylalkyl, a substituted or unsubstituted $C_3$-$C_{30}$ cycloalkenyl, a substituted or unsubstituted $C_5$-$C_{30}$ aryl, a substituted or unsubstituted a $C_5$-$C_{30}$ arylalkyl, a substituted or unsubstituted $C_5$-$C_{30}$ heteroaryl, a substituted or unsubstituted $C_3$-$C_{30}$ heterocyclic ring, a substituted or unsubstituted $C_4$-$C_{30}$ heterocyclylalkyl, a substituted or unsubstituted $C_6$-$C_{30}$ heteroarylalkyl; or $R^{26}$ and $R^{27}$ together with the carbon atom to which they are bonded are joined together to form a saturated or unsaturated ring optionally containing one or more heterocyclic atoms. In another embodiment, the ketones for use herein include those containing at least three carbon atoms. Representative examples of ketones for use herein include, but are not limited to, acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone, methyl sec butyl ketone, methyl tert-butyl ketone, ethyl butyl ketone, ethyl isobutyl ketone, ethyl sec-butyl ketone, ethyl tert-butyl ketone, propyl butyl ketone, isopropyl butyl ketone, propyl isobutyl ketone, propyl sec-butyl ketone, propyl tert butyl ketone, isopropyl isobutyl ketone, isopropyl sec-butyl ketone, isopropyl tert-butyl ketone, dibutyl ketone, diisobutyl ketone, di-sec-butyl ketone, di-tert-butyl ketone, butyl isobutyl ketone, butyl sec-butyl ketone, butyl tert-butyl ketone, isobutyl sec-butyl ketone, isobutyl tert-butyl ketone, sec-butyl tert-butyl ketone, 5-heptanone, 5-methyl-2-hexanone (methyl isoamyl ketone), 4-methyl-2-hexanone, 3-methyl-2-hexanone, 3,4-dimethyl-2-pentanone, 3,3-dimethyl-2-pentanone, 4,4-dimethyl-2-pentanone, 3-octanone, 4-methyl-3-heptanone, 5-methyl-3-heptanone, 6-methyl-3-heptanone, 4,4-dimethyl-3-hexanone, 4,5-dimethyl-3-hexanone, 5,5-dimethyl-3-hexanone, 4-nonanone, 5-methyl-4-octanone, 6-methyl-4-octanone, 7-methyl-4-octanone, 5,5-dimethyl-4-neptanone, 5,6-dimethyl-4-heptanone, 6,6-dimethyl-4-heptanone, 2-undecanone, cyclopropanone, cyclobutanone, cyclopentanone, cyclohexanone, cycloheptanone, cyclooctanone, cyclononanone, cyclodecanone, cycloundecanone, cyclododecanone and the like and combinations thereof. A preferred ketone for use herein is acetone.

Suitable alcohols for use herein include, but are not limited to, $C_1$-$C_{30}$ aliphatic alcohols, $C_6$-$C_{30}$ aromatic alcohols and the like and mixtures thereof. Examples of useful alcohols include, but are not limited to, methyl alcohol, ethyl alcohol, propyl alcohol, isopropyl alcohol, butyl alcohol, benzyl alcohol and the like and mixtures thereof. A preferred alcohol for use herein is isopropyl alcohol.

Suitable ether solvents for use herein include, but are not limited to, tetrahydrofuran and the like and mixtures thereof. Suitable aliphatic hydrocarbon solvents for use herein include, but are not limited to, hexane, heptane, and the like and mixtures thereof. Suitable aromatic hydrocarbon solvents for use herein include, but are not limited to, toluene, benzene, xylene and the like and mixtures thereof. Suitable sulfoxide solvents for use herein include, but are not limited to, dimethylsulfoxide (DMSO), sulfolane and the like and mixtures thereof. Suitable amide-based solvents for use herein include, but are not limited to, pyrrolidine, dimethylformamide (DMF), dimethylacetamide (DMA) and the like and mixtures thereof.

Generally, the amount of solvent employed in the solution will range from about 5% w/w to about 500% w/w and preferably from about 10% w/w to about 200% w/w.

Next, the polymerization product will be taken out of the solution and the solvent will be substantially removed from the swelled polymerization product to provide the drug delivery system of the present invention. The solvent can be substantially removed from the swelled polymerization product by techniques known in the art such as, for example, drying, e.g., air drying, vacuum drying, freeze drying, drying under an inert gas (e.g., nitrogen), in an oven at elevated temperatures and the like.

In an alternate embodiment, the drug delivery systems of the present invention can be prepared by polymerizing the monomeric mixture under polymerization conditions as discussed above in the presence of one or more pharmaceutically active agents such that the pharmaceutically active agent(s) is entrapped in the polymerization product. As one skilled in the art will readily appreciate, the resulting polymerization product may have some pharmaceutically active agent(s) which is covalently bound to the polymerization product as well as some free starting monomer(s). If desired, these reactants may be removed from the resulting product by conventional techniques.

The matrix controlled diffusion drug delivery systems of the present invention may be manufactured in any suitable form, shape, e.g., circular, rectangular, tubular, square and triangular shapes, or size suitable for the treatment which they are intended to be used. Methods of forming the subject matrix controlled diffusion drug delivery systems include, but are not limited to, cast molding, injection/compression molding, extrusion, and other methods known to those skilled in the art. The drug delivery systems of the present invention are advantageously sized and configured for back of the eye delivery, e.g., for use as an inner back of the eye implant such as a hollow cylinder or tube having a first cross dimension (diameter and width), ranging from about 1 mm to about 5 mm and a second cross dimension, such as length, from about 0.2 mm to about 10 mm.

Alternatively, the drug delivery system can be in the form of a solution, suspension, solution/suspension, microsphere or nanosphere using a pharmaceutically acceptable carrier well known in the art. Additionally, the solution, suspension, solution/suspension, microsphere or nanosphere can contain one or more pharmaceutically acceptable excipients such as suspending agents, e.g., sodium carboxymethyl cellulose, methylcellulose, hydroxypropylmethylcellulose, sodium alginate, poly(N-vinylpyrrolidone), gum tragacanth and gum acacia; dispersing or wetting agents, e.g., naturally occurring phosphatide, e.g., lecithin, or condensation products of an alkylene oxide with fatty acids, e.g., polyoxyethylene stearate, or condensation products of ethylene oxide with long chain aliphatic alcohols, e.g., heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Once manufactured, the subject matrix controlled diffusion drug delivery systems are packaged and sterilized using customary methods known to those skilled in the art.

Matrix controlled diffusion drug delivery systems of the present invention may be used in a broad range of therapeutic applications. The matrix controlled diffusion drug delivery systems of the present invention are particularly useful in the treatment of ophthalmic diseases, disorders and/or injuries. Representative examples of such ophthalmic diseases, disorders or injuries include, but are not limited to, diabetic retinopathy, glaucoma, macular degeneration, retinitis pigmentosa, retinal tears or holes, retinal-detachment, retinal ischemia, acute retinopathies associated with trauma, inflammatory mediated degeneration, post-surgical complications, damage associated with laser therapy including photodynamic therapy (PDT), surgical light induced iatrogenic retinopathy, drug-induced retinopathies, autosomal dominant optic atrophy, toxic/nutritional amblyopias; leber's hereditary optic neuropathy (LHOP), other mitochondrial diseases with ophthalmic manifestations or complications, angiogenesis; atypical RP; bardet-biedl syndrome; blue-cone monochromacy; cataracts; central areolar choroidal dystrophy; choroideremia; cone dystrophy; rod dystrophy; cone-rod dystrophy; rod-cone dystrophy; congenital stationary night blindness; cytomegalovirus retinitis; diabetic macular edema; dominant drusen; giant cell arteritis (GCA); goldmann-favre dystrophy; graves' ophthalmopathy; gyrate atrophy; hydroxychloroquine; iritis; juvenile retinoschisis; kearns-sayre syndrome; lawrence-moon bardet-biedl syndrome; leber congenital amaurosis; lupus-induced cotton wool spots; macular degeneration, dry form; macular degeneration, wet form; macular drusen; macular dystrophy; malattia leventinese; ocular histoplasmosis syndrome; oguchi disease; oxidative damage; proliferative vitreoretinopathy; refsum disease; retinitis punctata albescens; retinopathy of prematurity; rod monochromatism; RP and usher syndrome; scleritis; sector RP; sjogren-larsson syndrome; sorsby fundus dystrophy; stargardt disease and other retinal diseases.

The drug delivery systems of the present invention can be administered to a mammal in need of treatment by way of a variety of routes. For example, the drug delivery systems may be used by implantation within a portion of the body in need of localized drug delivery, e.g., the interior portion of an eye. However, the subject matrix controlled diffusion drug delivery systems may likewise be used in accordance with other surgical procedures known to those skilled in the field of ophthalmology. For example, the drug delivery systems can be administered to the region of the eye in need of treatment employing instruments known in the art, e.g., a flexible microcatheter system or cannula disclosed in U.S. Patent Application Publication No. 2002/0002362, or the intraretinal delivery and withdrawal systems disclosed in U.S. Pat. Nos. 5,273,530 and 5,409,457, the contents of each which are incorporated by reference herein. The pharmaceutically active agent may be released from the drug delivery device over a sustained and extended period of time. Optionally, the drug release rate may also be controlled through the attachment of an inert diffusion barrier by way of, for example, surface treatment of the drug delivery device. The surface treatment may be applied through a variety of surface treatment techniques known in the art, e.g., oxidative plasma, evaporative deposition, dip coating or extrusion techniques.

The following examples are provided to enable one skilled in the art to practice the invention and are merely illustrative of the invention. The examples should not be read as limiting the scope of the invention as defined in the claims.

EXAMPLE 1

Synthesis of 1,3-bis(4-methacryloyloxybutyl)tetramethyl disiloxane ($M_2$)

To a four neck resin flask equipped with a mechanical stirrer, Dean-Stark trap, heating mantle, water cooled condenser and thermometer was added 1,1-dimethyl-1-sila-2-oxacyclohexane, methacrylic acid, and concentrated sulfuric acid. To the reaction mixture was then added cyclohexane and hydroquinone as a polymerization inhibitor. The reaction mixture was heated to reflux for five hours during which time of water was collected. The reaction mixture was then cooled, divided, and passed through two chromatography columns filled with alumina (packed using cyclohexane as eluant). The cyclohexane was removed using a rotary evaporator and the resultant $M_2$ is placed under vacuum for one hour at 80° C.

EXAMPLE 2

Synthesis of a methacrylate-terminated siloxane ($M_2D_2$)

To a round bottom flask under dry nitrogen was added $D_4$ (octamethylcyclotetrasiloxane) and the $M_2$ prepared in Example 1. Trifluoromethane sulfonic acid was added as initiator. The reaction mixture was stirred 24 hours with vigorous stirring at room temperature. Sodium bicarbonate is then added and the reaction mixture was again stirred for 24 hours. The resultant solution was filtered through a 0.3μ Teflon® filter. The filtered solution was vacuum stripped and placed under vacuum (>0.1 mm Hg) at 50° C. to remove the unreacted silicone cyclics. The resulting methacrylate terminated siloxane was a viscous, clear fluid.

EXAMPLE 3

To 100 parts of the methacrylate terminated siloxane prepared in Example 2 (where x=2) was added 1.0% Irgacure 819 as a photoinitiator and 20% w/w of fluocinolone acetonide (FA). The suspension was added to Teflon tubes (0.5 mm in diameter) available from Boramed (Durham, N.C.) and polymerized using visible light polymerization techniques. The cure conditions consisted of two hours of visible light irradiation. Following the cure the drug loaded copolymer was removed from tube resulting in a release device having dimensions of 5 mm by 0.5 mm.

EXAMPLE 4

Drug Release

The sample as prepared in Example 3 was placed in 3 cc of borate buffer in a sealed glass tube and the amount of FA release is monitored at 34° C. At periodic intervals, 3 cc of solution is removed and replaced with 3 cc of fresh borate. The solution is analyzed by liquid chromatography (LC) for FA. The release rate per day and percent cumulative release were determined. A zero-order drug release is obtained shortly after the initial burst as shown in FIG. 1 for $M_2D_2$ (200A).

EXAMPLE 5

Synthesis of a methacrylate-terminated siloxane ($M_2D_{50}$)

To a round bottom flask under dry nitrogen was added $D_{50}$ and the $M_2$ prepared in Example 1. Trifluoromethane sulfonic acid was added as initiator. The reaction mixture was stirred 24 hours with vigorous stirring at room temperature. Sodium bicarbonate is then added and the reaction mixture was again stirred for 24 hours. The resultant solution was filtered through a 0.3μ Teflon® filter. The filtered solution was vacuum stripped and placed under vacuum (>0.1 mm Hg) at 50° C. to remove the unreacted silicone cyclics. The resulting methacrylate terminated siloxane was a viscous, clear fluid.

EXAMPLE 6

To 100 parts of the methacrylate terminated siloxane prepared in Example 5 was added 1.0% Irgacure 819 as a photoinitiator and 20% w/w of FA. The suspension was added to Teflon tubes (0.5 mm in diameter) available from Boramed (Durham, N.C.) and polymerized using visible light polymerization techniques. The cure conditions consisted of two hours of visible light irradiation. Following the cure the drug loaded copolymer was removed from tube resulting in a release device having dimensions of 5 mm by 0.5 mm.

EXAMPLE 7

Drug Release

Figure 2:
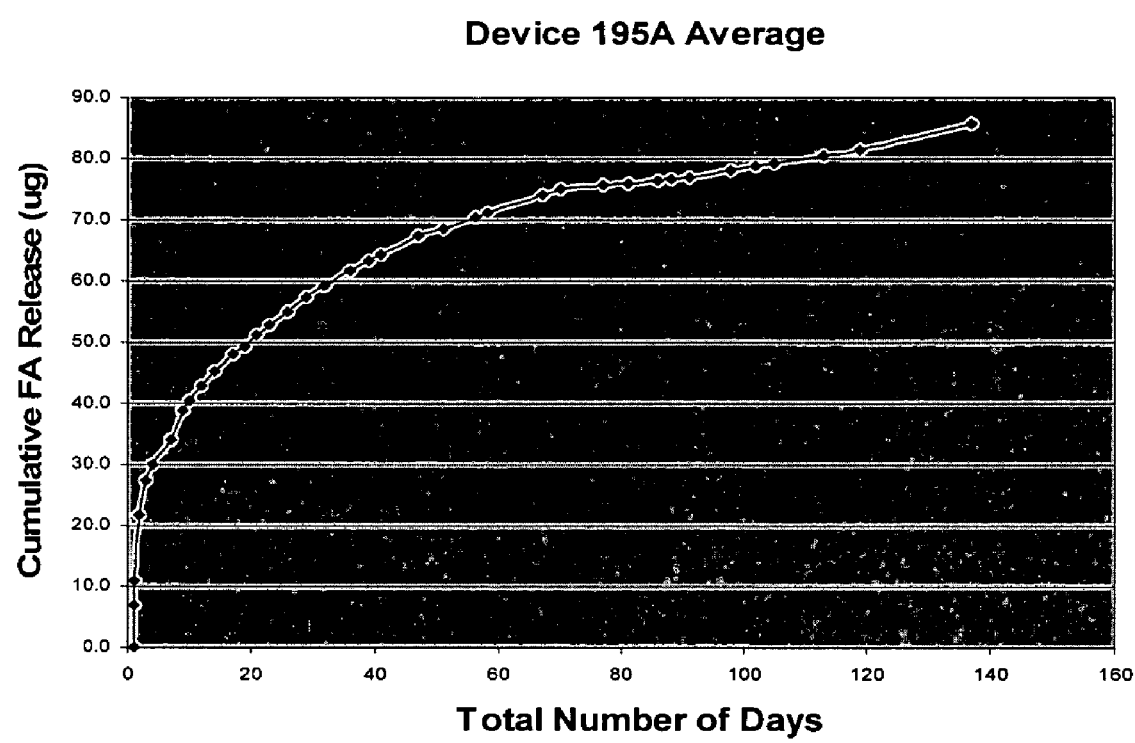
FIG. 2 is a graphical representation depicting the percent cumulative drug release rate over time for a $M_2D_{50}$ (195A) siloxane loaded with 30% w/w fluocinolone acetonide.

The sample as prepared in Example 6 was placed in 3 cc of borate buffer in a sealed glass tube and the amount of FA release was monitored at 34° C. At periodic intervals, 3 cc of solution is removed and replaced with 3 cc of fresh borate. The solution was analyzed by LC for FA. The release rate per day and percent cumulative release were determined. A zero-order drug release was obtained shortly after the initial burst as shown in FIG. 2 for $M_2D_{50}$ (195A).

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A matrix controlled diffusion drug delivery system comprising a therapeutically effective amount of one or more pharmaceutically active agents entrapped in a polymerization product of a monomeric mixture comprising one or more silicone-containing monomers of the general formula:

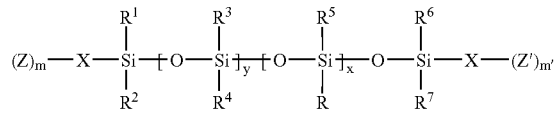

wherein x and y are independently integers from 0 to about 300; m and m' are independently integers from 1 to about 6, R is independently a straight or branched, substituted or unsubstituted, $C_1$-$C_{30}$ alkyl group, a $C_1$-$C_{30}$ fluoroalkyl group, an ether or polyether containing group or a $C_1$-$C_{30}$ alkylamide group, $R^1$, $R^2$, $R^3$, $R^4$, $R^5$, $R^6$ and $R^7$ are independently hydrogen, a straight or branched $C_1$-$C_{30}$ alkyl group, a $C_1$-$C_{30}$ fluoroalkyl group, a $C_1$-$C_{20}$ ester group, an alkyl ether, cycloalkyl ether, cycloalkylalkyl ether, cycloalkenyl ether, aryl ether, arylalkyl ether or polyether containing group, an ureido group, an amide group, an amine group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocyclolalkyl group, a substituted or unsubstituted $C_6$-$C_{30}$ heteroarylalkyl group, fluorine, a vinyl group, a $C_5$-$C_{30}$ fluoroaryl group, or a hydroxyl group; X is independently a straight or branched $C_1$-$C_{30}$ alkyl group, a $C_1$-$C_{30}$ fluoroalkyl group, a substituted or unsubstituted $C_5$-$C_{30}$ arylalkyl group, a substituted or unsubstituted $C_1$-$C_{30}$ alkoxy group, an ether, polyether, sulfide, or amino containing group and Z and Z' are independently a polymerizable ethylenically unsaturated organic radical, wherein the matrix controlled diffusion drug delivery system is sized and configured for back of the eye delivery.

2. The matrix controlled diffusion drug delivery system of claim 1, wherein x is 2 to about 100, y is 2 to about 100, $R^1$, $R^2$, $R^3$, $R^4$, $R^5$, $R^6$ and $R^7$ are independently a straight or branched $C_1$-$C_{30}$ alkyl group, and Z and Z' are selected from an ester or amide of acrylic or methacrylic acid.

3. The matrix controlled diffusion drug delivery system of claim 1, wherein x is 2 to about 100, y is 2 to about 100, $R^1$, $R^2$, $R^3$, $R^4$, $R^5$, $R^6$ and $R^7$ are independently a straight or branched $C_1$-$C_6$ alkyl group X is a bond or an ether or polyether containing group, and Z and Z' are independently an ester or amide of acrylic or methacrylic acid.

4. The matrix controlled diffusion drug delivery system of claim 1, wherein x is 2 to about 100, y is 2 to about 100, R is independently a straight or branched $C_1$-$C_{30}$ fluoroalkyl group, an alkyl ether or polyether group or a straight or branched $C_1$-$C_{30}$ alkylamide group, $R^1$, $R^2$, $R^3$, $R^4$, $R^5$, $R^6$ and $R^7$ are independently a straight or branched $C_1$-$C_6$ alkyl group, X is independently a bond or one or more $C_1$-$C_{30}$ alkyl ether groups or polyether groups and Z and Z' are independently an ester or amide of acrylic or methacrylic acid.

5. The matrix controlled diffusion drug delivery system of claim 1, wherein the one or more pharmaceutically active agents is selected from the group consisting of an anti-glaucoma agent, anti-cataract agent, anti-diabetic retinopathy agent, thiol cross-linking agent, anti-cancer agent, immune modulator agent, anti-clotting agent, anti-tissue damage agent, anti-inflammatory agent, anti-fibrous agent, non-steroidal anti-inflammatory agent, antibiotic, anti-pathogen agent, piperazine derivative, cycloplegic agent, miotic agent, mydriatic agent and mixtures thereof.

6. The matrix controlled diffusion drug delivery system of claim 1, wherein the one or more pharmaceutically active agents is selected from the group consisting of an anticholinergic, anticoagulant, antifibrinolytic, antihistamine, antimalarial, antitoxin, chelating agent, hormone, immunosuppressive, thrombolytic, vitamin, protein, salt, desensitizer, prostaglandin, amino acid, metabolite, antiallergenic and mixtures thereof.

7. The matrix controlled diffusion drug delivery system of claim 1, wherein the monomeric mixture comprises one or more other monomers or prepolymers.

8. The matrix controlled diffusion drug delivery system of claim 7, wherein the one or more monomers are selected from the group consisting of methyl methacrylate, 2-ethylhexyl methacrylate, benzyl methacrylate, 2-phenylethyl methacrylate, dimethyl itaconate, trifluoromethyl methacrylate, hexafluoroisopropyl methacrylate, bis(hexafluoroisopropyl) methacrylate, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, acrylic acid, itaconic acid, acrylic anhydride, methacrylic anhydride, maleic anhydride, itaconic anhydride, glycerol methacrylate, hydroxypropyl methacrylate, N,N-dimethylacrylamide, acrylamide, N-methylacrylamide, N-vinylpyrrolidione, N-isopropylacrylamide, hydroxybutyl methacrylate and mixtures thereof.

9. The matrix controlled diffusion drug delivery system of claim 1, in a form of a solution, suspension, solution/suspension, microsphere or nanosphere.

10. The matrix controlled diffusion drug delivery system of claim 1, in a form of a semi-solid or solid article suitable for ocular implant.

* * * * *